United States Patent [19]

Barber et al.

[11] Patent Number: 5,626,146

[45] Date of Patent: May 6, 1997

[54] ELECTRICAL IMPEDANCE TOMOGRAPHY

[75] Inventors: David C. Barber, Sheffield; Brian H. Brown, Holmesfield, both of England

[73] Assignee: British Technology Group Limited, London, England

[21] Appl. No.: 454,137

[22] PCT Filed: Dec. 16, 1993

[86] PCT No.: PCT/GB93/02564

§ 371 Date: Jun. 8, 1995

§ 102(e) Date: Jun. 8, 1995

[87] PCT Pub. No.: WO94/15228

PCT Pub. Date: Jul. 7, 1994

[30] Foreign Application Priority Data

Dec. 18, 1992 [GB] United Kingdom .............. 9226376

[51] Int. Cl.$^6$ .............................. G06F 15/42; G06F 17/00; A61B 5/05
[52] U.S. Cl. ........................................................ 128/734
[58] Field of Search ............................................... 128/734

[56] References Cited

U.S. PATENT DOCUMENTS 4,263,920  4/1981  Tasto et al. .
4,486,835  12/1984  Bai et al. .
4,539,640  9/1985  Fry et al. ........................ 128/734
4,617,939  10/1986  Brown et al. .

FOREIGN PATENT DOCUMENTS 9119454  12/1991  WIPO .
9302617  2/1993  WIPO .

OTHER PUBLICATIONS

Smith et al, "Digital demodulator for electrical impedence monitoring" IEEE Enginering in Medicine & Biology 11th Annual Conference, 1989 pp. 1744–1745 vol. 6.

Primary Examiner—Vincent Millin
Assistant Examiner—Robert N. Wieland
Attorney, Agent, or Firm—Cushman, Darby & Cushman Ip Group of Pillsbury Madison & Sutro LLP

[57] ABSTRACT

To improve the reliability of the image or to selectively enhance parts of the image produced by way of a tomographic technique such as electrical impedance tomography (EIT), also known as applied potential tomography (APT), the method and apparatus of the invention provides that the electrical signal measurements be made over varying periods of time. The manner of variation can be related to the relative positions of drive and receive electrode pairs or to the output signal size, either as theoretically expected or as actually measured. The invention can be applied to serial or to parallel data collection techniques.

8 Claims, 3 Drawing Sheets

ELECTRICAL IMPEDANCE TOMOGRAPHY

BACKGROUND TO THE INVENTION

This invention relates to tomography and more particularly to the technique known variously as electrical impedance tomography or applied potential tomography referred to hereinafter as EIT.

EIT involves the production of images representing the distribution of an electrical characteristic, such as electrical conductivity or resistivity, across a sectional plane of a body under investigation from measurements made on the periphery of the sectional plane. The technique finds application in non-invasive investigation of human patients, but may be applied to investigation of animals or of other bodies, such as geological masses. It is a relatively inexpensive method of tomography, allows continuous monitoring, and does not suffer from the biological hazards implicit in other procedures such as X-ray computed tomography. The technique is described in, for example, a paper entitled "Applied potential tomography" by D. C. Barber and B. H. Brown published in J.Phys.E: Sci.Instrum., Vol.17 (1984), pages 723–733, and in other papers referred to therein or published subsequently.

In a typical application of EIT to a body an array of, say, sixteen electrodes is placed around the periphery of a body section such as the thorax. Electrical currents, from a constant current source of a few milliamps at a fixed frequency, are applied in turn to adjacent pairs of the electrodes (known as 'drive pairs') and for each applied current the real component of the potential difference is measured between the thirteen adjacent pairs of the fourteen other electrodes (known as 'receive pairs'). Further measurements between non-adjacent electrode pairs are not required, as they would not represent independent data but could be obtained by linear combinations of the adjacent measurements. It is of course to be noted that drive pairs and receive pairs need not necessarily be made up of adjacent electrodes and that other combinations of electrodes can be used to gather the set of independent data. The resulting set of voltages from all thirteen receive pairs is referred to as a 'data profile'. The measured values from all such data profiles are stored and processed to create a two-dimensional image of the resistivity distribution within the body. A static image may be created, showing the absolute value of tissue resistivity, or a dynamic image may be produced, displaying the changes in resistivity from a reference. The latter is the more clinically useful as changing features of the body such as cardiac activity and lung activity can be monitored.

The EIT image is reconstructed by assuming the measurements have been taken around the periphery of a two dimensional homogenous circular conducting plane. The measured values are filtered to correct for blurring inherent in the imaging process and then backprojected along lines of backprojection to allow determination of the resistivity values within the conducting image plane. The final reconstructed image can then be displayed, the speed of image production depending on the data handling capacity of the image reconstruction system. The technique of backprojection is described more fully in U.S. Pat. No. 4,617,939, to which reference can be made for further details.

The resolution of the image is restricted by the number of independent measurements available, in other words, by the number of electrodes employed. To improve image reconstruction speed, transputers are used for digital signal processing. In addition, the measurements of the voltages in all receive pairs can be made in parallel. Such parallel data collection allows each measurement to be made over a longer period and hence to a higher accuracy. Further details of this system can be found in WO91/19454.

The image reconstruction technique briefly described above produces clinically valuable images. However, it is widely recognised that the reliability of the image is not constant over the entirety of the image plane because of the remoteness of the measuring points from the centre of the body section. The greatest uncertainty is found in the centre of the reconstructed image, since small errors in boundary measurements cause large errors in the reconstructed image data in that central area. In consequence, the signal-to-noise ratio (SNR) of the image is relatively high adjacent to the periphery and decreases towards the centre of the image. As a result, it is difficult to reliably detect small changes in the centre of the image.

SUMMARY OF THE INVENTION

It is an object of the present invention to reduce the above-mentioned problem and to selectively enhance the image quality of part of an image and to this end there is provided according to one aspect of the invention a method of data collection for use in the construction of a tomographic image of a body comprising:

placing a plurality of electrodes adjacent the surface of the body at spaced intervals on the body;

applying, in successive manner through the electrodes, an electrical input signal to at least one electrode pair to generate a potential difference between other electrode pairs, and measuring at the said other electrode pairs; and measuring, at the said other electrode pairs and at each stage of the successive application of input signal, output signals representing an electrical characteristic of that body subjected to each applied input signal, wherein the measurements are made over varying periods of time.

In one embodiment, the period of time over which each measurement is made is selected according to the relative positions of the electrode pair at which the signal is measured and the electrode pair at which the electrical input signal is applied. Preferably, for the purposes of time weighting, the period of time over which each measurement is made is selected according to a theoretically expected signal size based on said relative positions.

Alternatively, the period of time over which each measurement is made is selected according to the size of the measured output signal.

The manner of variation of the measurement time periods is chosen to improve image quality in a preselected part of the image.

For each stage of the successive application of input signal the output signals at the other electrode pairs may be measured in parallel.

In the case of parallel data collection, it is preferred that the applied input signals are applied simultaneously at different electrode pairs at different frequencies, whilst the output signals are measured simultaneously at selected other electrode pairs at corresponding frequencies.

According to another aspect of the invention there is provided apparatus for data collection for use in the construction of a tomographic image of a body comprising:

a plurality of electrodes applicable adjacent the surface of the body at spaced intervals on the body;

means for applying, in successive manner through the electrodes, an electrical input signal to at least one electrode pair to generate a potential difference between the other electrode pairs; and means for measuring, at the other electrode pairs and at each stage of the successive application of the input signal, output signals representing an electrical characteristic of the body subjected to each respective applied input signal, wherein said means for measuring comprises means for varying the periods of time over which the measurements are made.

A longer period of measurement can therefore be used for the smaller signals, and this results in the noise element of the signal, which is a random fluctuation, being reduced, as the measurement recorded represents an average over that period. If the noise is Gaussian then the SNR will improve in proportion to the square root of the integration time. For small signals, lower noise levels are obtained and thus, in the case of a substantially circular body section, say, more accurate measurements representing information about the centre of the image are made.

SPECIFIC DESCRIPTION

Certain embodiments of the invention will now be described by way of example with reference to the accompanying drawings, in which.

Figure 1:
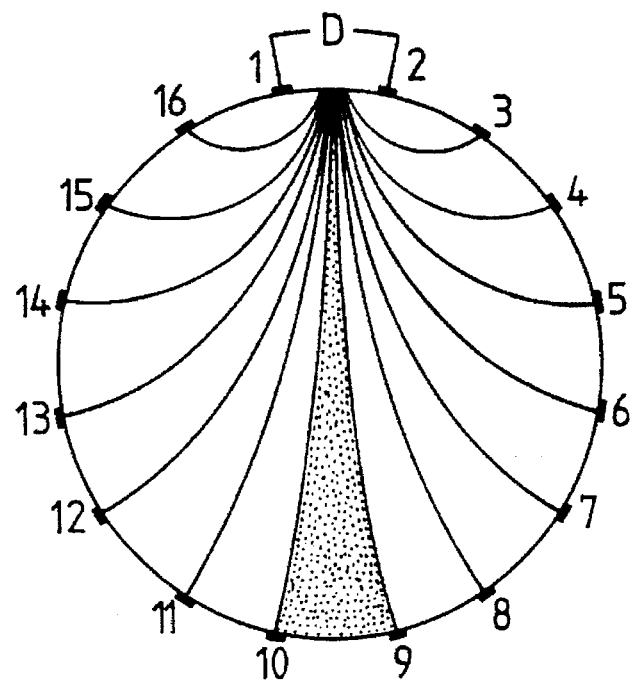
FIG. 1 illustrates the technique of backprojection in EIT.

FIG. 1 illustrates the technique of back projection as applied to a circular plane of uniform conductivity with 16 electrodes regularly spaced around its periphery. The curved lines represent isopotentials for the electrode drive pair 1/2, shown as a dipole D, and it is along such lines that actual measured signals can be backprojected to locate the resistivity values at points within the plane. Once all the measurements have been made for all the alternative drive pairs, and the data filtered, the resistivity images from each data profile are produced and superimposed in a weighted manner to create the image data.

Of course, other methods of image reconstruction other than that referred to above and illustrated in FIG. 1 are possible, and it is to be understood that the applicability of the present invention is in no way limited to any particular technique of reconstruction that may be used.

Figure 2:
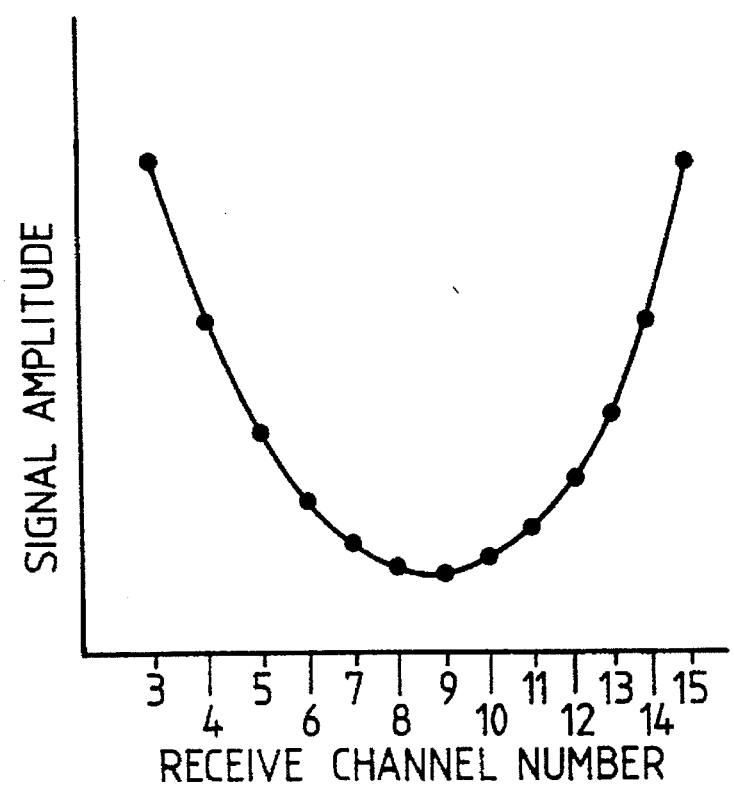
FIG. 2 shows the distribution of signal amplitudes received at different receive pairs as a result of a signal applied at one drive pair.

Clearly when the uniform circular plane of FIG. 1 is considered the signal amplitude measured at the different electrodes will be a function of the distance from the drive pair, the weakest signal being that detected at the electrodes on the opposite side of the circular plane. This distribution of signal amplitudes is represented in the graph of FIG. 2, the signal amplitude being shown on the vertical axis and the electrode position around the circumference of the circular plane being shown on the horizontal axis, channel number 1 representing the receive pair 1/2, and so on.

As a result of this uneven distribution of signal amplitudes, and assuming uniform noise from the different measurements, the signal-to-noise ratio (SNR) is correspondingly lower for those measurements made on the opposite side of the circular plane from the drive pair, such as electrodes 9 and 10 in this example. Actual measured signals representing resistivity information about points within the body plane in the area shown shaded in FIG. 1 will have the lowest SNR. As can be seen this area includes the central region of the plane and more peripheral parts of this shaded area. As the other adjacent pairs of electrodes are subsequently used as drive pairs more information is gathered about the more peripheral areas of the plane, but points within the more central region of the body plane always result in detected signals having the lowest SNR. This is the reason for high noise and hence low signal reliability for pixels within the central region of the image.

By making use of the method of the invention the SNR can be increased for this central region by spending a longer period of time making each measurement if that measurement contains information about the central region. In other words, within each data profile the period of time over which each measurement is made, or dwell time, is dependent on the electrode pair position where the measurement is made. The total time for gathering the data profile is maintained by correspondingly reducing the dwell time for receive pairs close to the drive pair, and therefore at least partially balancing the SNR across the image.

The most basic EIT data collection system involves serial data collection, whereby, for each data profile, measurements are made from the receive pairs in a sequence progressing around the circumference. This is accomplished by switching the inputs to amplifiers of the data acquisition system according to a stored switching sequence. Using such a system the invention is utilised by programming a new switching sequence, the dwell times being determined from, say, the theoretical signal amplitude distribution of FIG. 2, such that the data collection interval is proportional to the inverse of the theoretical signal amplitude and the total data collection time is substantially unchanged. The technique requires no new equipment over that conventionally used for EIT systems, but simply requires a modified switching sequence.

In actual fact, two factors dominate the unequal SNR across an EIT image. The dynamic range of the signals is one factor, and the other is the weighting process implicit in the reconstruction algorithm. Modifying the dwell times according to the theoretical signal amplitudes will not in fact equalise the noise distribution across the image, due to this second factor. However in practice modifying the dwell times even in this simple manner does produce a considerable improvement in image quality in the central region of the image.

As an example, a 50 kHz signal is supplied from a controlled current source with a constant peak-to-peak amplitude of 5 mA. To achieve a image display speed of 25 frames per second a frame interval of 40 ms is required. For a sixteen electrode system each data profile must therefore be collected in 2.5 ms, allowing an average dwell time of 192 µs for each measurement. By modifying this dwell time depending on the position of the receive pair relative to the drive pair by a factor determined by, say, the theoretical signal amplitude as explained above, the equalisation of the noise elements of each data profile can be significantly improved.

More recent EIT data collection systems involve parallel data collection to increase the speed of data acquisition. In such systems a constant current generator is multiplexed between adjacent electrode pairs and differential amplifiers are placed between all such electrode pairs, allowing simultaneous collection of data from each data profile. In this way, for a certain frame interval, a longer dwell time is available for each voltage measurement.

Using such a system the invention can be utilised by successively reallocating amplifiers to more remote pairs as they are switched out from the more adjacent ones, in a sequence selected to collect the data in the most efficient way whilst ensuring the desired dwell times are maintained for each measurement. In this way two or more amplifiers are used to make measurements of the smaller signals, whereas only one would be used to measure the largest signals. When the entire image set is collected, the SNR of the data containing information about the more central regions of the body will therefore be higher.

Alternatively a multifrequency system is employed using interleaved drive and receive pairs. With this system, each drive pair and each receive pair is operable at any one of a number of frequencies. Measurements can therefore be made in parallel between different drive and receive pairs by operating simultaneously at the different frequencies.

For example, in a 16 electrode system electrode pairs 1/3, 3/5, 5/7 etc. can each be arranged to be driven at any one of a number of eight frequencies f1 to f8. Electrode pairs 2/4, 4/6, 6/8 etc. can be used as receive pairs each at any one of frequencies f1 to f8. The data collection is made as follows:

| Drive | Receive |
| --- | --- |
| 1/3 at f1 | 4/6 at f1 |
| 3/5 at f2 | 6/8 at f2 |
| 5/7 at f3 | 8/10 at f3 |
| ↓ | ↓ |
| 15/1 at f8 | 2/4 at f8 |

The above represents a single period of measurement, and since all the corresponding drive and receive pairs are separated by a relatively short peripheral distance the signals will be large and a short dwell time can be selected. The next data collection set is made as follows:

| Drive | Receive |
| --- | --- |
| 1/3 at f1 | 6/8 at f1 |
| 3/5 at f2 | 8/10 at f2 |
| 5/7 at f3 | 10/12 at f3 |
| ↓ | ↓ |
| 15/1 at f8 | 4/6 at f8 |

These will be smaller signals so a longer dwell time is selected. The process is continued, each data collection period being used to measure signals in parallel from drive pairs and receive pairs separated by the same peripheral distance, and the dwell time for each collection period being predetermined according to this distance. The final data collection set of the above sequence will be as follows:

| Drive | Receive |
| --- | --- |
| 1/3 at f1 | 14/16 at f1 |
| 3/5 at f2 | 16/2 at f2 |
| 5/7 at f3 | 2/4 at f3 |
| ↓ | ↓ |
| 15/1 at f8 | 12/14 at f8 |

The data collection time for this final set will be the same as that for the first set of the sequence as the drive pair-receive pair separation is identical.

This technique gives a complete data set of 384 (8*8*6) measurements. Separate generators are required for each of the drive pairs, but the system does not involve the switching of amplifiers from one electrode pair to another, merely the switching of frequencies received at different times.

The methods of data collection described above suggest modifying the dwell time for each measurement, according to the position of the receive pair relative to the drive pair, by an amount determined by the theoretical signal size. Alternatively, the dwell time for each measurement can be controlled on the basis of the amplitude of each signal as measured, as it has been observed that theoretical and measured signals can differ, especially where the expected signal is large.

A series of experiments was conducted by the inventors to investigate the spatial distribution of noise in images from a saline-filled tank and to test a noise equalisation method according to the invention, such method depending on choosing a longer dwell time for smaller signals.

Test data was collected from a circular cylindrical saline filled tank with 16 brass electrodes equally spaced around its circumference. The tank diameter was approximately 152 mm. The saline solution extended 155 mm above and 90 mm below the electrode plane with 2 mS/cm conductivity at 25C.

Two groups of tank data were collected for both the noise distribution study and the equalisation experiments. Each group of data contained 6000 frames of 104 measurements collected at 25 frames per second. The first group of data was collected from the saline filled tank without any object and the second data set with a plastic rod (10 mm diameter) introduced at 38 mm from the edge of the tank.

The noise distribution of both the measured voltages and the reconstructed image pixels was determined by calculating the root-mean-square (RMS) noise and the signal-to-noise ratio.

The noise distribution of the measurements of voltage between the electrodes around the tank was calculated as the ratio of the standard deviation to the mean of the measurements of each voltage difference over the 6000 frames of the first group of data. It was found that the SNR on the smallest voltage measurements was about 10 dB worse than that of the largest voltage measurements. The largest voltages are those recorded close to the electrodes through which current is being injected and the smallest are those on the other side of the tank.

Having reconstructed the frames as images, using the first frame as a reference, the RMS noise at each of the 16 pixels across a diameter of the images was computed as the standard deviation of the pixel value over the 6000 images. Two image reconstruction algorithms were used, referred to henceforth as the Mk 1 and the Mk 2 algorithms. The Mk. 1 algorithm is described in Barber D C and Brown B H, 1986, Recent developments in applied potential tomography, information Processing in Medical Imaging, ed. S Bacharach (Dordrecht: Martinus Nijhoff), pp 106–21, whilst the Mk 2 algorithm is described in Barber D C and Brown B H, 1990, Progress in electrical Impedance tomography, Inverse Problems in Partial Differential Equations, ed. D Colton, R Ewing and W Rundell (Philadelphia: SIAM), pp 151–64, and in Barber D C and Brown B H, 1990, Reconstruction of impedance images using filtered back projection, Proc. CAIT Meeting on Electrical Impedance Tomography (Copenhagen), pp 108. These two reconstruction algorithms differ in that the second gives a better and more uniform point response function than the first. Results showed that the RMS noise at the centre was about 20.4 dB and 29.5 dB worse than at the edge when using the Mk 1 and Mk 2 reconstruction algorithms respectively.

In order to find out how uniform the image noise would be with perfect data, 6000 frames with added noise to give a standard deviation of 0.1 on all voltages were simulated. These frames were reconstructed to produce 6000 images using both the Mk 1 and Mk2 reconstruction algorithms. By measuring the RMS noise on the 16 pixels crossing the diameter, it was seen that the noise on the central pixels was about 3 times and 10 times higher than on the edge pixels, when using the Mk 1 and Mk 2 reconstruction algorithms respectively. It was concluded that the unequal distribution of noise in images from the tank is caused both by variations in SNR on the measured voltages and on the image reconstruction algorithm used. It might also be inferred that there is a distribution of signal to noise ratios on the measured voltages which would give rise to uniform noise in the reconstructed images.

Various ways of implementing noise equalisation were then tried and the results compared. It was found that a ratio of 49 to 1 (Table 1) between the dwell times for the smallest and largest signals respectively gives a large improvement in the image noise uniformity but the noise is still worse in the middle than at the edge of the image. Larger ratios could be used but these may not be practical. A ratio of about 49 to 1 is a realistic ratio that could be implemented on a serial data collection system running at 10 frames per second by spending about 30 µs on the large measurements and 1500 µs on the small ones. As most EIT systems use frequencies of about 50 kHz with a period of 20 µs, larger ratios would not give enough time to make the larger measurements. Also, for a 49 to 1 ratio, it was found that the SNR improvement was almost linearly proportional to the square root of the collection time, but for much larger ratios this was not the case because the noise is not strictly Gaussian.

TABLE 1

RESULTS OF NOISE EQUALISATION SCHEME

| Y | DATA SET Dwell Time | IMAGE SNR Improvement (Theoretical) | IMAGE SNR Improvement (Measured) |
|---|---|---|---|
| 1 largest | 1 | 0 dB edge | 0 dB edge |
| 2 | 4 | 6.0 dB | 5.9 dB |
| 3 | 9 | 9.5 dB | 9.5 dB |
| 4 | 16 | 12.0 dB | 11.9 dB |
| 5 | 25 | 14.0 dB | 13.8 dB |
| 6 | 36 | 15.6 dB | 15.4 dB |
| 7 smallest | 49 | 16.9 dB centre | 16.5 dB centre |

This shows the results of applying noise equalisation to images reconstructed using the Mk 1 algorithm. Y lists the measurements from the largest (adjacent to the current injection pair) to the smallest (on the opposite side of the tank). The system uses 16 electrodes such that one profile is of 13 measurements. By varying the dwell times as shown an increasing improvement in SNR is obtained from the edge to the centre of the image.

Using a ratio of 49 to 1 the improvement in central noise is 16.5±0.3 dB and 15.6±0.4 dB using the Mk 1 and Mk 2 reconstruction algorithms respectively. After noise equalisation, the RMS noise at the image centre relative to that at the edge drops from 15 to 2.2 times and from 30 to 5.0 times when using the Mk 1 and Mk 2 reconstruction algorithms respectively. It is difficult to produce a completely uniform noise distribution but it is possible to make a very significant improvement in the noise uniformity.

FIGS. 3 and 4 show the results of noise equalisation on the images of the plastic rod in the tank, using the equalisation scheme shown in Table 1, with Mk 1 and Mk 2 reconstruction algorithms respectively.

Figure 3A:
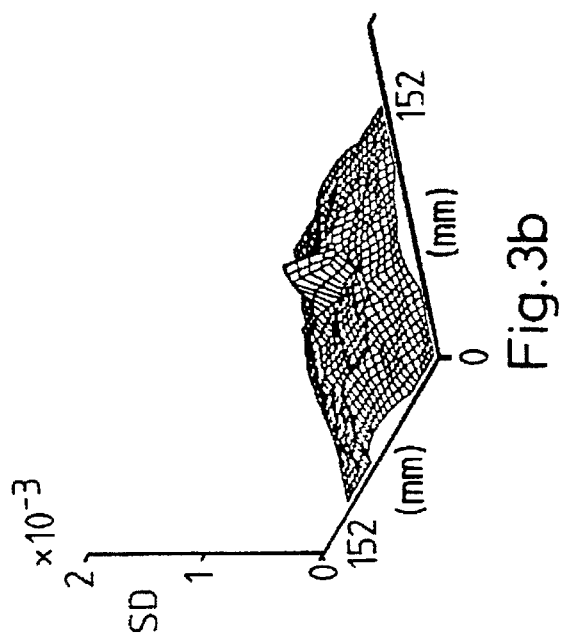
FIGS. 3a to 3d illustrate the performance of the method of the invention on data from a saline-filled tank containing a plastic rod using one image reconstruction algorithm.
Figure 3B:
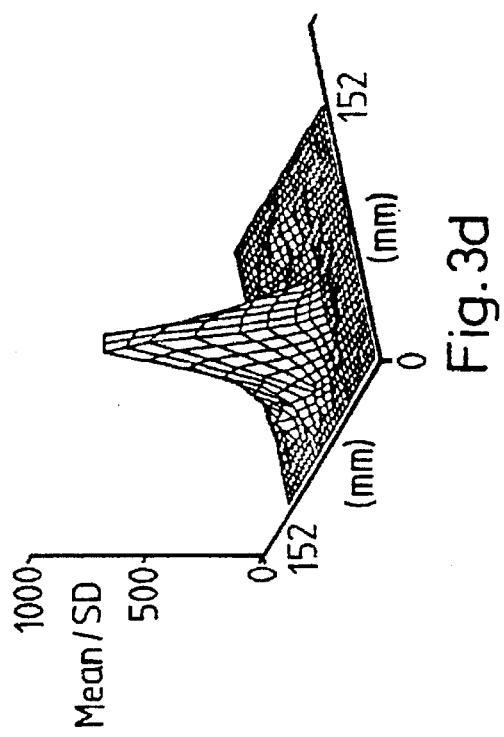
Figure 3C:
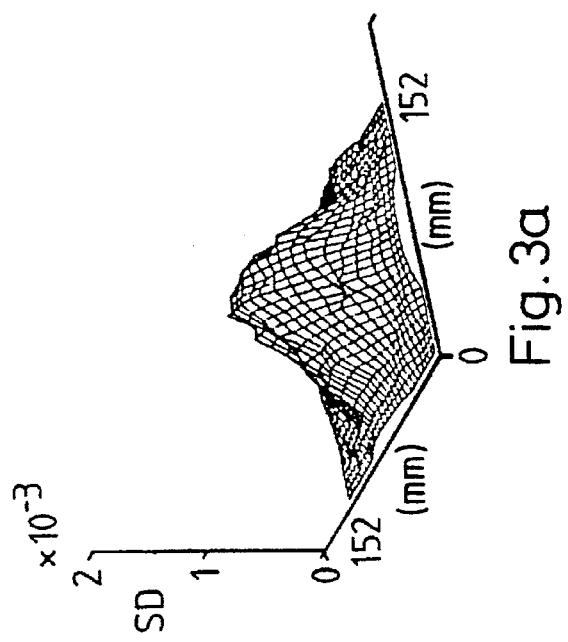
Figure 3D:
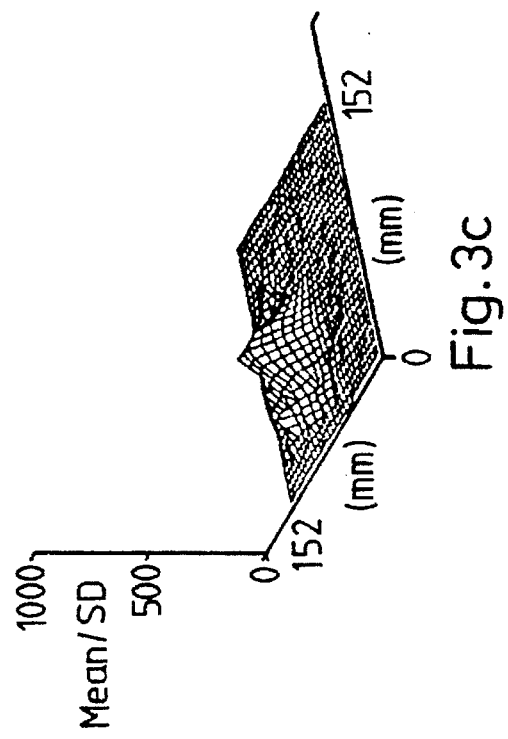
Figure 4B:
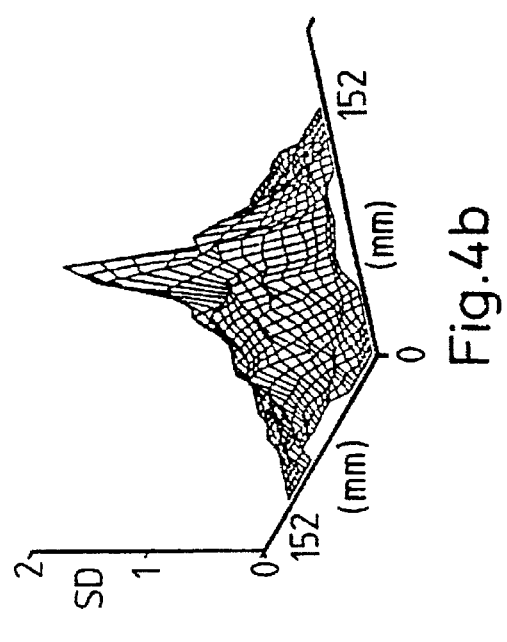
FIGS. 4a to 4d correspond to FIGS. 3a to 3d, but illustrate the use of an alternative image reconstruction algorithm.
Figure 4D:
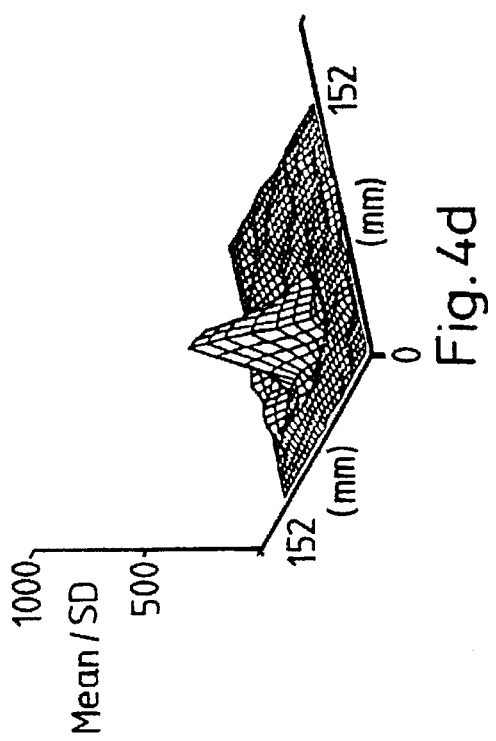
Figure 4A:
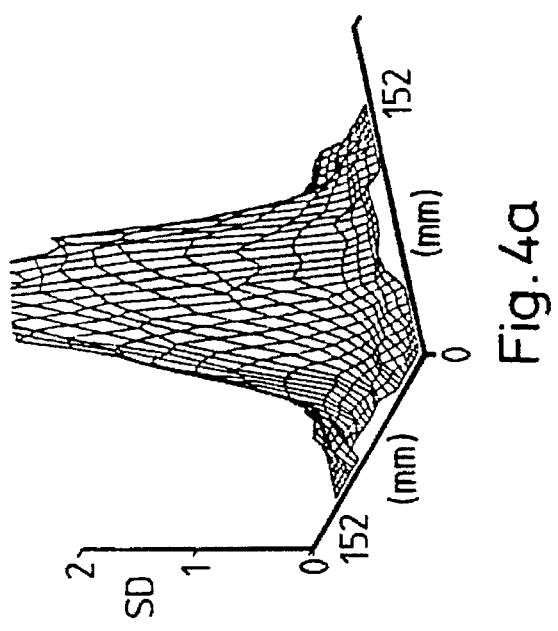
Figure 4C:
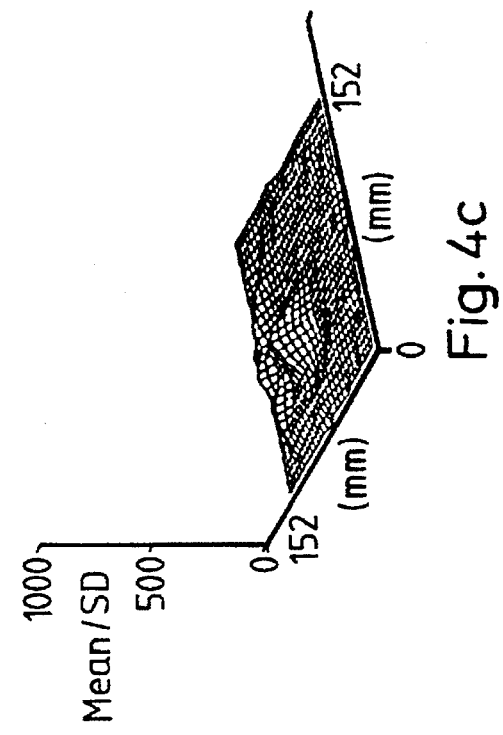

FIG. 3a shows the standard deviation over the images before the equalisation, whilst FIG. 3(b) shows that after the equalisation. FIG. 3(c) shows the SNR before the equalisation whilst FIG. 3(d) shows that after the equalisation For a particular pixel, the SNR is given by the mean signal value divided by the standard deviation. The improvement in the SNR over the central region is very clear. FIGS. 4(a) to 4(d) show equivalent spatial plots for images reconstructed using the Mk 2 algorithm. Again, the improvement in the SNR is clear, but the noise distribution is in fact less uniform than in FIG. 3. These figures illustrate the significance of the reconstruction algorithm and show how the weighting implicit in the algorithm can affect the uniformity of noise across the image.

It is further possible using the method of the invention to specifically alter the dwell times in order to target selected areas of the image and thereby increase the SNR and enhance the image in that selected area. For example, at the expense of image quality in other parts of the image, the distribution of dwell times can be computed to specifically target the lungs.

The embodiments of the invention described above are given by way of example only and it should be understood that these are not intended in any way to limit the scope of the invention.

We claim:

1. A method of data collection for use in the construction of a tomographic image of a body comprising:

placing a plurality of electrodes adjacent the surface of the body at spaced intervals on the body;

applying, in successive manner through the electrodes, an electrical input signal to at least one electrode pair to generate a potential difference between other electrode pairs; and measuring, at the said other electrode pairs and at each stage of the successive application of input signal, output signals representing an electrical characteristic of that body subjected to each applied input signal, wherein the measurements are made over varying periods of time.

2. A method according to claim 1, wherein the period of time over which each measurement is made is selected according to the relative positions of the electrode pair at which the signal is measured and the electrode pair at which the electrical input signal is applied.

3. A method according to claim 2, wherein, for the purposes of time weighting, the period of time over which each measurement is made is selected according to a theoretically expected signal size based on said relative positions.

4. A method according to claim 1, wherein the period of time over which each measurement is made is selected according to the size of the measured output signal.

5. A method according to claim 1 wherein the manner of variation of the measurement time periods is chosen to improve image quality in a preselected part of the image.

6. A method according to claim 1 wherein for each stage of the successive application of input signal the output signals at the other electrode pairs are measured in parallel.

7. A method according to claim 6 wherein the applied input signals are applied simultaneously at different electrode pairs at different frequencies, whilst the output signals are measured simultaneously at selected other electrode pairs at corresponding frequencies.

8. Apparatus for data collection for use in the construction of a tomographic image of a body comprising:

a plurality of electrodes applicable adjacent the surface of the body at spaced intervals on the body;

means for applying, in successive manner through the electrodes, an electrical input signal to at least one electrode pair to generate a potential difference between the other electrode pairs: and means for measuring, at the other electrode pairs and at each stage of the successive application of the input signal, output signals representing an electrical characteristic of the body subjected to each respective applied input signal, wherein said means for measuring comprises means for varying the periods of time over which the measurements are made.

* * * * *